US00PP22789P2

(12) United States Plant Patent
van den Top

(10) Patent No.: US PP22,789 P2
(45) Date of Patent: Jun. 12, 2012

(54) ***HOSTA* PLANT NAMED 'SECRET TREASURE'**

(50) Latin Name: ***Hosta* hybrid**
Varietal Denomination: Secret Treasure

(76) Inventor: Hendrik Jan van den Top, Barneveld (NL)

( * ) Notice: Subject to any disclaimer, the term of this patent is extended or adjusted under 35 U.S.C. 154(b) by 0 days.

(21) Appl. No.: 12/927,115

(22) Filed: Nov. 5, 2010

(51) Int. Cl.
*A01H 5/00* (2006.01)

(52) U.S. Cl. ..... Plt./353

(58) Field of Classification Search ..... Plt./353
See application file for complete search history.

*Primary Examiner* — Susan McCormick Ewoldt
(74) *Attorney, Agent, or Firm* — C. A. Whealy

(57) ABSTRACT

A new and distinct cultivar of *Hosta* plant named 'Secret Treasure', characterized by its outwardly spreading foliage with upright flower scapes; dark green and white variegated leaves; purple-colored flowers that are positioned above the foliar plane on strong scapes; and good garden performance.

2 Drawing Sheets

Botanical designation: *Hosta* hybrid.
Cultivar denomination: 'SECRET TREASURE'.

BACKGROUND OF THE INVENTION

The present invention relates to a new and distinct cultivar of *Hosta* plant, botanically known as *Hosta* hybrid and hereinafter referred to by the name 'Secret Treasure'.

The new *Hosta* plant is a naturally-occurring whole plant mutation of the *Hosta* hybrid 'One Man's Treasure', not patented. The new *Hosta* plant was discovered and selected by the Inventor in a controlled outdoor nursery environment in Barneveld, The Netherlands during the spring of 2008.

Asexual reproduction of the new *Hosta* plant by divisions in a controlled outdoor nursery environment in Barneveld, The Netherlands since July, 2008 has shown that the unique features of this new *Hosta* plant are stable and reproduced true to type in successive generations.

SUMMARY OF THE INVENTION

Plants of the new *Hosta* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Secret Treasure'. These characteristics in combination distinguish 'Secret Treasure' as a new and distinct cultivar of *Hosta* plant:

1. Outwardly spreading foliage with upright flower scapes.
2. Dark green and white variegated leaves.
3. Purple-colored flowers that are positioned above the foliar plane on strong scapes.
4. Good garden performance.

Plants of the new *Hosta* differ primarily from plants of the parent, 'One Man's Treasure', primarily in leaf color as plants of 'One Man's Treasure' do not have variegated leaves.

Plants of the new *Hosta* can be compared to plants of 'Sweet Innocence', not patented. Plants of the new *Hosta* and 'Sweet Innocence' differ primarily in leaf coloration as plants of 'Sweet Innocence' have light green and pale yellow variegated leaves.

BRIEF DESCRIPTION OF THE PHOTOGRAPHS

The accompanying colored photographs illustrate the overall appearance of the new *Hosta* plant showing the colors as true as it is reasonably possible to obtain in colored reproductions of this type. Colors in the photographs may differ slightly from the color values cited in the detailed botanical description which accurately describe the colors of the new *Hosta* plant.

The photograph on the first sheet comprises a side perspective view of a typical flowering plant of 'Secret Treasure' grown in a container.

The photograph on the second sheet is a close-up view of a typical inflorescence of 'Secret Treasure'.

DETAILED BOTANICAL DESCRIPTION

The aforementioned photographs and following observations, measurements and values describe plants grown during the late summer/early autumn in two-liter containers in an outdoor nursery in Barneveld, The Netherlands and under commercial practice. Plants were 14 months old when the photographs and description were taken. In the following description, color references are made to The Royal Horticultural Society Colour Chart, 2001 Edition, except where general terms of ordinary dictionary significance are used.

Botanical classification: *Hosta* hybrid 'Secret Treasure'.

Parentage: Naturally-occurring whole plant mutation of the *Hosta* hybrid 'One Man's Treasure', not patented.

Propagation:

*Type.*—By divisions.

*Root description.*—Medium in thickness, fibrous; creamy white in color.

*Rooting habit.*—Moderate branching; medium density.

Plant description:

*Plant form/habit.*—Herbaceous flowering perennial plant; mounded plant form with outwardly spreading foliage and upright flower scapes; flowering stems and leaves basal; moderately vigorous growth habit; purple-colored flowers that are positioned above the foliar plane on strong scapes.

*Growth rate.*—Moderately fast; about one year is required to produce fully-grown flowering plants.

*Plant height* (*soil level to top of foliar plane*).—About 15 cm.

*Plant height* (*soil level to top of inflorescences*).—About 45 cm.

*Plant width* (*spread*).—About 40 cm.

Foliage description:

*Arrangement/form.*—Leaves basal, simple, generally symmetrical and long-persisting.

*Leaf length.*—About 12 cm to 18 cm.

*Leaf width.*—About 7 cm to 9 cm.

*Shape.*—Cordate.

*Apex.*—Cuspidate to caudate.

*Base.*—Truncate to rounded.

*Margin.*—Entire.

*Texture, upper and lower surfaces.*—Smooth, glabrous; leathery; moderately rugose.

*Venation pattern.*—Pinnate, arcuate.

*Color.*—Developing leaves, upper surface: Center, close to 137C; towards the margins, close to 8D. Developing leaves, lower surface: Center, more green than 146A; towards the margins, close to 155A. Fully expanded leaves, upper surface: Center, close to N137A; towards the margins, close to 155A; venation, similar to surface colors. Fully expanded leaves, lower surface: Center, close to 137C; towards the margins, close to 155B; venation, similar to surface colors.

*Petiole length.*—About 10 cm to 13 cm.

*Petiole diameter.*—About 4 mm to 6 mm.

*Petiole texture, upper and lower surfaces.*—Smooth, glabrous.

*Petiole color, upper and lower surfaces.*—Center, close to 137C with random spots, close to 187A, towards the margins, close to 155A with random spots, close to 187A.

Flower description:

*Flower type/habit.*—Single campanulate flowers with fused perianth arranged on terminal racemes; flowers face mostly outwardly; panicles narrowly conical in shape; freely flowering habit.

*Fragrance.*—Moderately fragrant; sweet, pleasant. Natural flowering season: Flowering recurrent during August and September in The Netherlands.

*Postproduction longevity.*—Flowers last about one week on the plant; flowers not persistent.

*Flower buds.*—Height: About 1.5 cm to 3.5 cm. Diameter: About 4 mm to 11 mm. Shape: Ovate. Color: Close to N77C.

*Inflorescence height.*—About 14 cm to 18 cm.

*Inflorescence diameter.*—About 8 cm to 10 cm.

*Flower diameter.*—About 3.5 cm.

*Flower depth.*—About 4.5 cm.

*Perianth.*—Arrangement: Three interior tepals arranged in a single whorl surrounded by an outer whorl of three exterior tepals. Tepal lobe length: About 1.2 cm to 1.4 cm. Tepal lobe width: About 0.9 cm to 1.2 cm. Tepal lobe shape: Ovate. Tepal apex: Acute. Tepal margin: Entire. Tepal texture, upper and lower surfaces: Smooth, glabrous; satiny. Tepal color: Developing and fully expanded petals, upper surface: Towards the apex, close to 76A; towards the center and base, close to N79D. Developing and fully expanded petals, lower surface: Close to N80C to N80D.

*Flower bracts.*—Quantity: One per flower at the base of the pedicel. Length: About 1.5 cm. Width: About 5 mm. Shape: Ovate. Apex: Acute. Margin: Entire. Texture, upper and lower surfaces: Smooth, glabrous. Color, upper and lower surfaces: Close to N77C.

*Peduncles* (*scapes*).—Length: About 30 cm to 45 cm. Diameter: About 4 mm to 5 mm. Angle: Erect. Strength: Strong. Texture: Smooth, glabrous. Color: Close to 200B tinted with a purplish hue.

*Pedicels.*—Length: About 1.5 cm. Diameter: About 1 mm. Strength: Strong. Texture: Smooth, glabrous. Color: Close to 151A.

*Reproductive organs.*—Stamens: Quantity per flower: Typically six; anthers dorsifixed. Stamen length: About 5 cm. Filament color: Close to 155C. Anther shape: Narrowly oblong. Anther length: About 2 mm. Anther color: Close to N187B. Pollen amount: Moderate. Pollen color: Close to N163D. Pistils: Quantity per flower: One. Style length: About 5 cm. Style color: Close to 155C. Stigma shape: Lobed. Stigma color: Close to 155C. Ovary length: About 5 mm. Ovary color: Close to N144A.

*Seed/fruit.*—Seed and fruit development have not been observed.

Disease/pest resistance: Plants of the new *Hosta* have not been noted to be resistant to pathogens and pests common to *Hosta*.

Garden performance: Plants of the new *Hosta* have been observed to have good garden performance and to tolerate rain, wind and temperatures ranging from about −30° C. to about 35° C.

It is claimed:

1. A new and distinct *Hosta* plant named 'Secret Treasure' as illustrated and described.

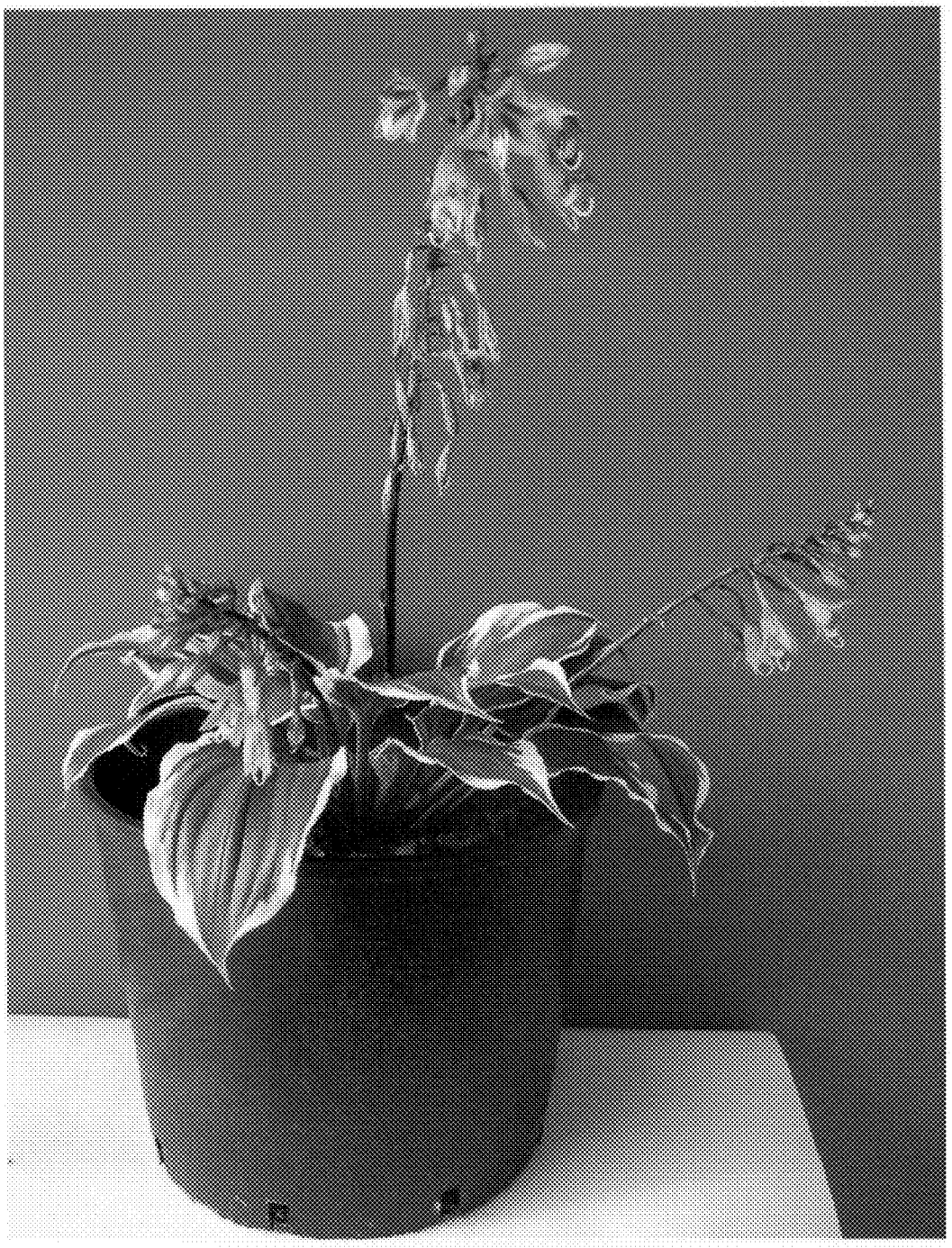

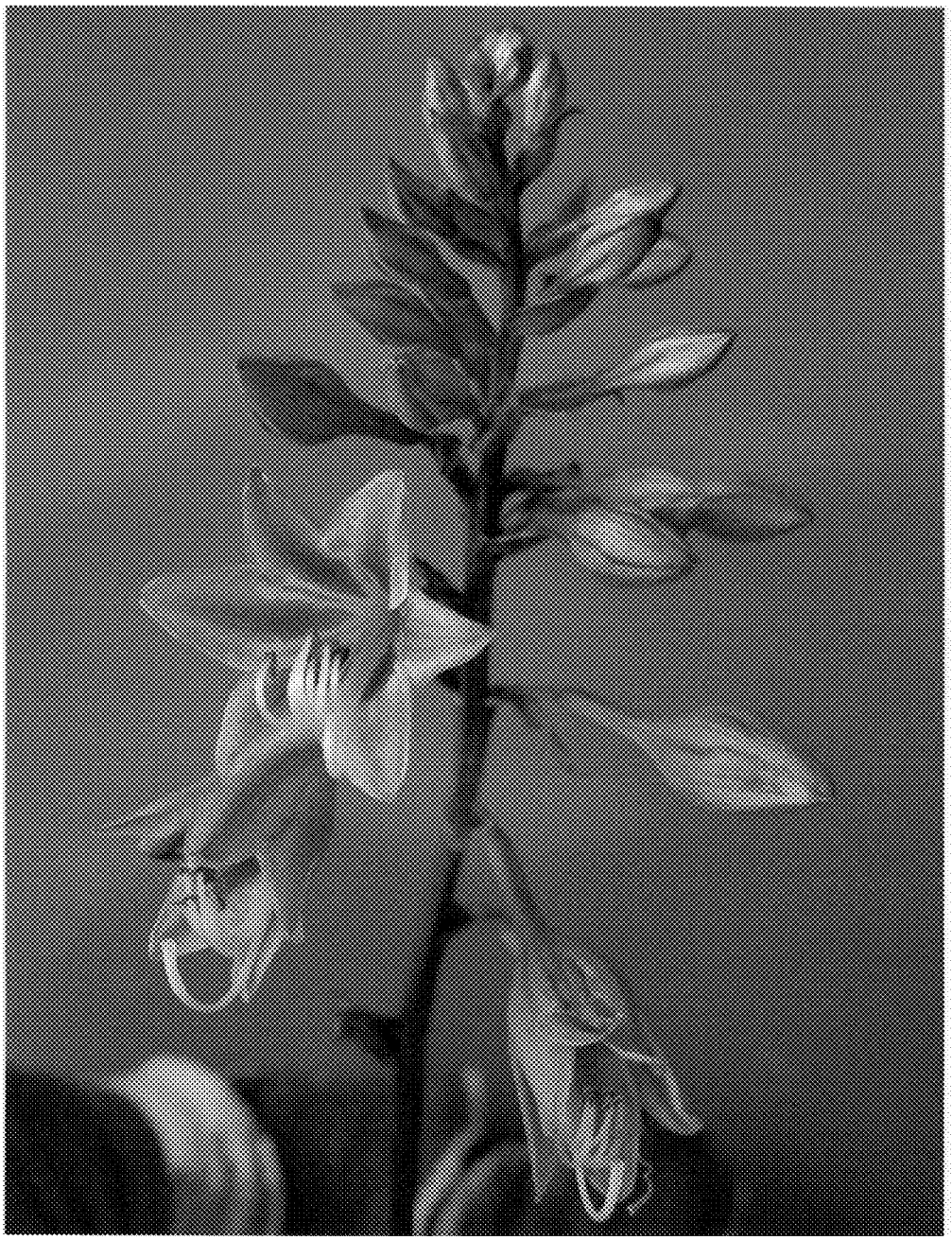

* * * * *